United States Patent [19]

Mullane

[11] Patent Number: 4,663,345

[45] Date of Patent: May 5, 1987

[54] ETODOLAC FOR TREATMENT OF GOUT

[75] Inventor: John F. Mullane, Westchester, N.Y.

[73] Assignee: American Home Products Corporation, New York, N.Y.

[21] Appl. No.: 853,069

[22] Filed: Apr. 17, 1986

[51] Int. Cl.⁴ .............................................. A61K 31/35
[52] U.S. Cl. ..................................................... 514/454
[58] Field of Search ......................................... 514/454

[56] References Cited

PUBLICATIONS

Chem. Abst., vol. 88 (1978)–83,363m.

Primary Examiner—Stanley J. Friedman

[57] ABSTRACT

A method is disclosed for lowering uric acid blood levels by administering an effective amount of etodolac.

4 Claims, No Drawings

ETODOLAC FOR TREATMENT OF GOUT

BACKGROUND OF THE INVENTION

1. Field of the Invention

This invention relates to a novel therapeutic use of 1,8-diethyl-1,3,4,9-tetrahydropyrano[3,4-b]indole-1-acetic acid whose generic name is etodolac. More specifically this invention relates to a method for lowering uric acid blood levels in humans for treatment of gout.

2. Prior Art

The active agent of this invention, 1,8-diethyl-1,3,4,9-tetrahydropyrano[3,4-b]indole-1-acetic acid or a therapeutically acceptable salt thereof, is disclosed in U.S. Pat. No. 3,939,178 issued Feb. 17, 1976. This active agent, hereinafter designated by its generic name etodolac, previously has been reported to be useful as an analgesic and anti-inflammatory agent. (See U.S. Pat. No. 3,939,178). I have now found unexpectedly that etodolac, either in its free acid form or in its therapeutically acceptable salt form, is useful for lowering uric acid blood levels in humans, and particularly humans suffering from gout.

This finding, coupled with the fact that etodolac is a relatively safe drug, renders the method of this invention particularly useful and advantageous.

SUMMARY OF THE INVENTION

According to this invention a method is provided for lowering uric acid blood levels in a human in need of said treatment, which comprises administering to the human an affective amount of etodolac, or a therapeutically acceptable salt thereof.

DETAILS OF THE INVENTION

According to the present method, etodolac, either in its free acid form or in the therapeutically acceptable salt form, is employed as the active agent. Examples of suitable salt forms are described in U.S. Pat. No. 3,939,178 and include the sodium, potassium, magnesium, triethylamine and benzylamine salt forms. A preferred salt form is the sodium salt, i.e. etodolac sodium.

Etodolac or a therapeutically acceptable addition salt thereof is administered to humans suffering from elevated uric acid blood levels, either orally or parenterally. For many reasons oral administration is preferred.

While etodolac or a therapeutically acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 3,939,178, herein incorporated by reference in its entirety.

When utilizing etodolac or one of its above-noted salts as agents for lowering uric acid blood levels, the total dose of active agent can range from about 50 milligrams to about 1000 milligrams per day with a preferred dosage range of from 200 to 600 milligrams per day. However, greater lowering of uric acid can be achieved with 1000 mg per day. Generally, a parenteral dose or an oral dose is administered in one to four applications per day, but more commonly twice a day. Such doses are considered to be an effective amount when, following their administration, a decrease in uric acid blood levels is experienced by the patient, or when the subjective symptoms complained of by said human beings are reported as having disappeared, or as being ameliorated or reduced in severity following such treatment.

The effectiveness of etodolac or its therapeutically acceptable salts as agents for lowering uric acid blood levels in a human has been demonstrated in human patients.

Three 6-week and four 12-week double blind clinical trials were conducted with patients suffering from rheumatoid arthritis or degenerative joint disease. A total of 711 patients received etodolac at a daily dose of 50 to 600 milligrams and 339 patients were receiving placebo.

The frequency distribution of daily dose by treatment group, i.e. how many patients received etodolac and in what amount is shown in the following Tables I and II.

TABLE I

Frequency Distibution of Prescribed Daily Dose by Treatment Group

| Etodolac, Milligrams | Number Of Patients* Four 12 Week Studies | | | |
|---|---|---|---|---|
| | 1 | 2 | 3 | 4 |
| 50 | 0 | 0 | 0 | 0 |
| 100 | 8 | 4 | 0 | 39 |
| 200 | 8 | 7 | 6 | 80 |
| 300 | 19 | 12 | 0 | 0 |
| 400 | 29 | 45 | 27 | 0 |
| 600 | 0 | 0 | 0 | 0 |

TABLE II

Frequency Distribution of Prescribed Daily Dose by Treatment Group

| Prescribed Daily Dose Etodolac, Milligrams | Number Of Patients* Three 6 Week Studies | | |
|---|---|---|---|
| | 1 | 2 | 3 |
| 50 | 56 | 0 | 45 |
| 100 | 55 | 0 | 43 |
| 200 | 49 | 44 | 44 |
| 300 | 0 | 0 | 0 |
| 400 | 0 | 91 | 0 |
| 600 | 0 | 0 | 0 |

*Patients missing uric acid levels not included in analysis

The Three 6-week and four 12-week double-blind studies were analyzed statistically to compare etodolac and placebo with respect to uric acid levels. The analysis included 688 patients (265 from the 12-week studies) receiving etodolac and the 339 placebo patients (200 from the 12-week studies). The variable of interest was each patient's average uric acid level within each of the following day range: baseline, days 1–27, days 28–55, days 56–83, and days 84–111.

Regression analysis revealed that in both the pool of 12-week studies and the pool of all studies, there was a significant difference between the etodolac group and the placebo group in the estimated slope of the relationship between uric acid and day range. In each case, the slope in the etodolac group was negative, indicating a decrease over time in uric acid levels, while the slope in the placebo group was positive.

Time-point analyses performed on the pool of all studies revealed that within each day range, there was a significant difference between etodolac and placebo in the mean change from baseline and in the proportion of patients who decreased from baseline. Within each day range, the etodolac group showed a mean decrease from baseline while the placebo group showed a mean increase from baseline; greater proportions in the etodolac group showed decreases. The mean changes in the etodolac group were between −0.05 mg uric acid per 100 milliliter of serum and −0.31 mg uric acid per 100 milliliter of serum; in the placebo group they were between 0.12 mg uric acid per 100 milliliters of serum and 0.23 mg uric acid per 100 milliliters of serum.

The results of the analysis of all 7 double-blind protocols were:

1. the etodolac slope was negative, −0.0872, and significantly different from zero, p=0.0015, 2. the placebo slope, 0.0478, was not significantly different from zero, p=0.1887, and 3. a significant difference between drug groups in slopes as indicated by the drug by day range interaction, p=0.0024.

The results are shown in Table III

TABLE III

| URIC ACID LEVELS | | | | |
|---|---|---|---|---|
| | Day Range | | | |
| | 0-27 | 28-55 | 56-83 | 84-111 |
| Ultradol | | | | |
| Baseline | | | | |
| mean | 5.20 | 5.26 | 5.23 | 5.03 |
| Standard | 1.66 | 1.59 | 1.42 | 1.32 |
| patients | 688 | 477 | 173 | 134 |
| Timepoint | | | | |
| mean | 5.15 | 5.03 | 4.91 | 4.81 |
| Standard | 1.48 | 1.50 | 1.27 | 1.27 |
| patients | 688 | 477 | 173 | 134 |
| Change | | | | |
| mean | −0.05 | −0.23 | −0.31 | −0.22 |
| Standard | 0.85 | 1.07 | 0.91 | 0.93 |
| patients | 688 | 477 | 173 | 134 |
| Placebo | | | | |
| Baseline | | | | |
| mean | 5.11 | 5.20 | 5.21 | 5.15 |
| standard | 1.61 | 1.63 | 1.59 | 1.63 |
| patients | 339 | 207 | 1.09 | 82 |
| Timepoint | | | | |
| mean | 5.34 | 5.43 | 5.33 | 5.34 |
| Standard | 1.55 | 1.61 | 1.64 | 1.79 |
| patients | 339 | 207 | 1.09 | 82 |
| Change | | | | |
| mean | 0.22 | 0.23 | 0.12 | 0.19 |
| standard | 0.83 | 0.95 | 0.84 | 0.94 |
| patients | 339 | 107 | 109 | 82 |
| P-value of drug group comparison | 0.0001 | 0.0001 | 0.0001 | 0.0078 |

The method of this invention is particularly beneficial for lowering uric acid blood levels in a patient suffering from gout. The lowering of the uric acid blood levels was is addition to the usual anti-inflammatory effect exhibited by etodolac.

In another study in which patients with rheumatoid arthritis received either 300 or 1000 mg per day etodolac, there was a greater reduction in uric acid blood levels with the higher dose. The 157 patients receiving 300 mg per day etodolac had a mean reduction in uric acid over 6 months of 0.47 mg per 100 milliliter wherein, the 105 patients receiving 1000 mg per day for 6 months had a mean reduction for uric acid levels of 1.47 mg per 100 milliliter.

I claim:

1. A method for lowering uric acid blood levels in a human in need of such treatment, which comprises administering to the human an effective amount of etodolac or a therapeutically acceptable salt thereof.

2. The method of claim 1 in which the effective amount of etodolac is within the range of from about 50 mg to about 1000 mg per day.

3. The method of claim 1 in which the effective amount of etodolac is within the range of 200 mg to 1000 mg per day.

4. The method of claim 1 in which the human being treated suffers from gout.

* * * * *